(12) United States Patent
May

(10) Patent No.: US 9,216,136 B2
(45) Date of Patent: Dec. 22, 2015

(54) APPARATUS AND METHOD FOR ADMINISTERING PAIN RELIEF

(76) Inventor: Clifford B. May, Clarksville, AR (US)

( * ) Notice: Subject to any disclaimer, the term of this patent is extended or adjusted under 35 U.S.C. 154(b) by 1673 days.

(21) Appl. No.: 12/027,477

(22) Filed: Feb. 7, 2008

(65) Prior Publication Data

US 2009/0204034 A1  Aug. 13, 2009

(51) Int. Cl.
*A61H 23/02* (2006.01)
*A61H 1/02* (2006.01)
*A61N 5/06* (2006.01)

(52) U.S. Cl.
CPC .......... *A61H 23/0245* (2013.01); *A61H 23/02* (2013.01); *A61H 1/0292* (2013.01); *A61H 2201/10* (2013.01); *A61H 2201/1604* (2013.01); *A61H 2201/165* (2013.01); *A61H 2201/1614* (2013.01); *A61H 2201/1623* (2013.01); *A61H 2205/028* (2013.01); *A61H 2205/062* (2013.01); *A61N 2005/0652* (2013.01)

(58) Field of Classification Search
CPC ............. A61H 2015/0071; A61H 2201/0188; A61H 2201/1607; A61H 2201/1604; A61H 2201/1616; A61H 2201/1614; A61H 2205/062
USPC ............. 601/1, 15, 18, 46, 48, 70–74, 78, 79
See application file for complete search history.

(56) References Cited

U.S. PATENT DOCUMENTS

| | | |
|---|---|---|
| 502,776 A | 8/1893 | Cheverell |
| 3,659,614 A | 5/1972 | Jankelson |
| 4,315,502 A | 2/1982 | Gorges |
| 4,920,466 A | 4/1990 | Liu |
| 4,979,502 A * | 12/1990 | Hunt ................. 601/15 |
| 5,086,788 A | 2/1992 | Castel et al. |
| 5,421,799 A * | 6/1995 | Rabin et al. ............ 601/71 |
| 5,611,771 A | 3/1997 | Taylor |
| 5,928,262 A * | 7/1999 | Harber .............. 606/204.35 |
| 6,007,501 A * | 12/1999 | Cabados et al. ........ 601/15 |
| 6,022,328 A | 2/2000 | Hailey |
| 6,132,392 A | 10/2000 | Stone |
| 6,554,787 B1 * | 4/2003 | Griffin et al. ........... 602/74 |
| 7,014,639 B2 | 3/2006 | Walneck et al. |
| 7,282,037 B2 * | 10/2007 | Cho ...................... 601/80 |
| 7,320,667 B1 * | 1/2008 | Hanna ................... 601/70 |
| 8,012,109 B1 * | 9/2011 | Lather, Sr. ............. 601/15 |
| 2002/0183665 A1 * | 12/2002 | Suh ...................... 601/84 |
| 2004/0171970 A1 | 9/2004 | Schleuniger et al. |
| 2004/0193001 A1 | 9/2004 | Miller |
| 2005/0027315 A1 | 2/2005 | Plateroti |
| 2006/0253051 A1 | 11/2006 | Milne et al. |
| 2007/0149905 A1 * | 6/2007 | Hanna ................... 601/79 |
| 2007/0203431 A1 | 8/2007 | Leta |

* cited by examiner

Primary Examiner — Rachel Young

(57) ABSTRACT

An apparatus for administering pain relief has at least one quartz crystal disposed proximate an energizable vibratory element in a support structure for positioning the quartz-crystal-and-vibratory-element combination proximate the head region of an individual. A pair of support structures each having a quartz-crystal-and-vibratory-element combination is mounted upon a shoulder harness in spaced-apart relationship with respect to one another. An energizable lighting structure having a substantially linear series of illuminating elements is disposed in an arced relationship with respect to the quartz-crystal-and-vibratory-element combination. In a method of administering pain relief the apparatus is positioned proximate the head region of an individual, and the vibratory element and the lighting structure are both energized.

28 Claims, 3 Drawing Sheets

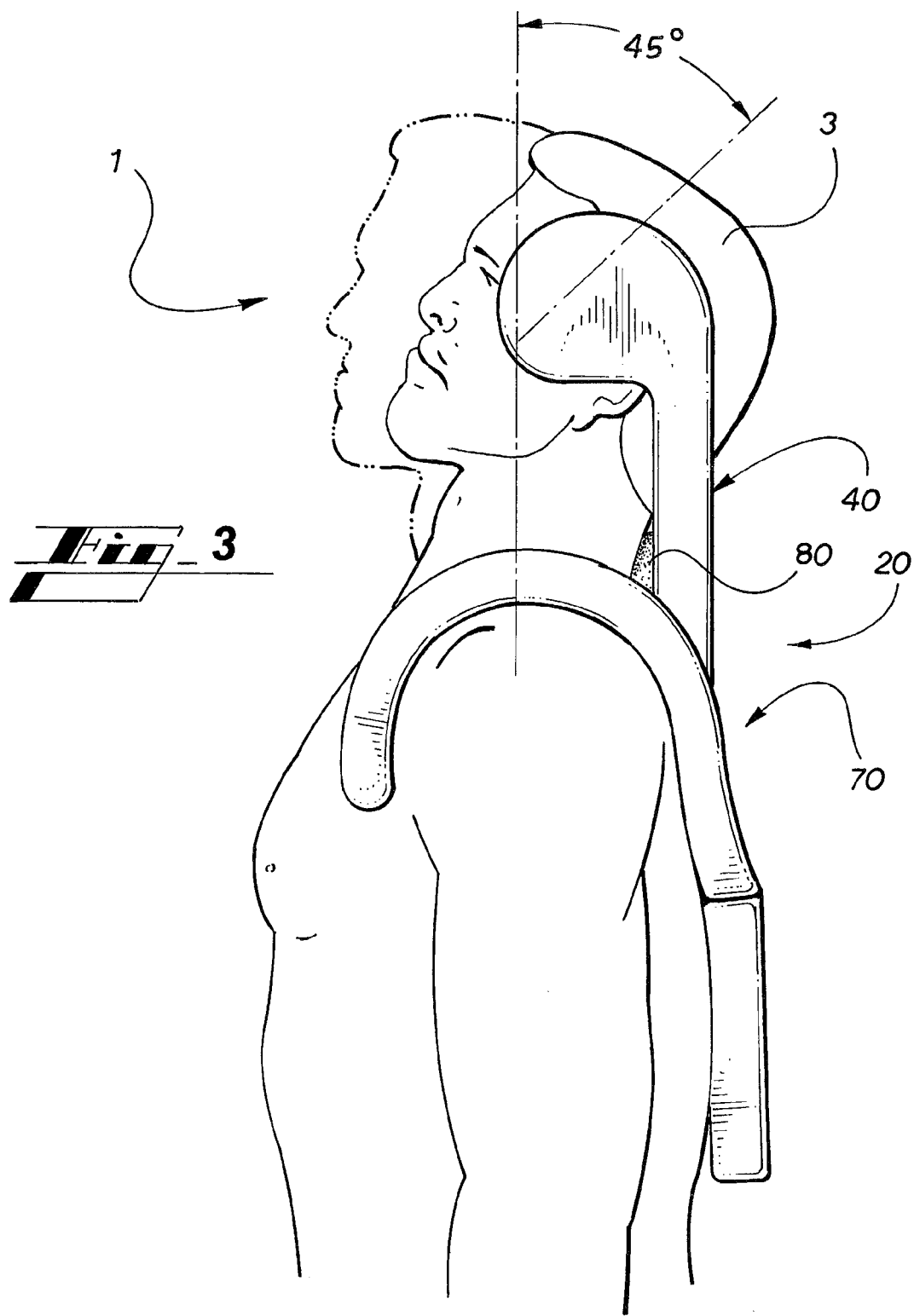

APPARATUS AND METHOD FOR ADMINISTERING PAIN RELIEF

TECHNICAL FIELD

This invention relates generally to devices for providing relief from pain to individuals. More specifically, the invention relates to an apparatus and a method for administering pain relief to the head region of an individual.

BACKGROUND OF THE INVENTION

Individuals often experience pain or discomfort in various parts of the body. Many individuals experience a type of pain commonly known as a headache. The origin of a headache is frequently unknown. An extremely severe type of headache known as a migraine is even more problematic for individuals. An individual typically desires relief from the pain of headache even if the precise cause is not known or treatable. Sometimes, treatment for headache pain can be as simple as resting, with varying degrees of success. Often individuals will consume over-the-counter or prescription medications to obtain relief from headache pain, with varying degrees of success. However, many individuals desire a reliable form of relief from headaches and other fairly minor manifestations of pain and discomfort that does not encompass taking medications.

SUMMARY OF THE INVENTION

The various embodiments of the present invention overcome the shortcomings of the prior art by providing at least one quartz crystal disposed proximate an energizable vibratory element. In a methodology employed, the quartz-crystal-and-vibratory-element combination is placed proximate the head region of an individual and the vibratory element is energized.

In an aspect of the invention, an energizable illumination structure is disposed proximate the quartz-crystal-and-vibratory-element combination.

Other systems, methods, features, and advantages of the present invention will be or become apparent to one with skill in the art upon examination of the following drawings and detailed description. All such additional systems, methods, features, and advantages are included within the scope of the present teaching and are protected by the accompanying claims.

The foregoing has broadly outlined some of the aspects and features of the present invention, which should be construed to be merely illustrative of various potential applications of the invention. Other beneficial results can be obtained by applying the disclosed information in a different manner or by combining various aspects of the disclosed embodiments. Accordingly, other aspects and a more comprehensive understanding of the invention may be obtained by referring to the detailed description of the exemplary embodiments taken in conjunction with the accompanying drawings, in addition to the scope of the invention defined by the claims.

BRIEF DESCRIPTION OF THE DRAWINGS

FIG. 3 is a perspective illustration of an exemplary embodiment of a method for administering pain relief utilizing the apparatus of FIG. 1.

DETAILED DESCRIPTION

Figure 1:
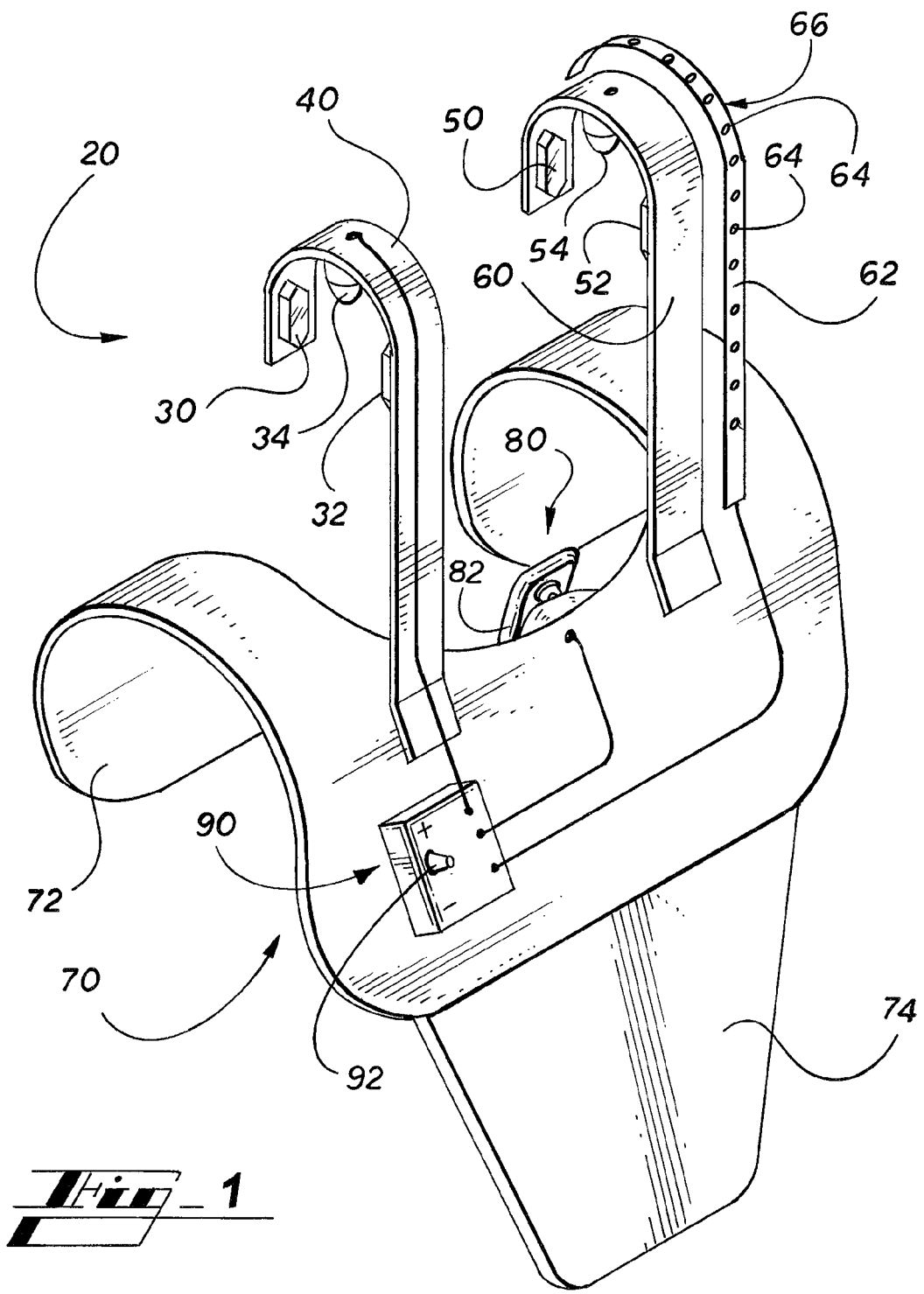
FIG. 1 is a perspective illustration of an exemplary embodiment of an apparatus for administering pain relief, according to the present invention.

As required, detailed embodiments of the present invention are disclosed herein. It must be understood that the disclosed embodiments are merely exemplary of the invention that may be embodied in various and alternative forms, and combinations thereof. As used herein, the word "exemplary" is used expansively to refer to embodiments that serve as illustrations, specimens, models, or patterns. The figures are not necessarily to scale and some features may be exaggerated or minimized to show details of particular components. In other instances, well-known components, systems, materials, or methods have not been described in detail in order to avoid obscuring the present invention. Therefore, specific structural and functional details disclosed herein are not to be interpreted as limiting, but merely as a basis for the claims and as a representative basis for teaching one skilled in the art to variously employ the present invention.

Referring now to the drawings, wherein like numerals indicate like elements throughout the several views, the drawings illustrate certain of the various aspects of exemplary embodiments.

Figure 2:
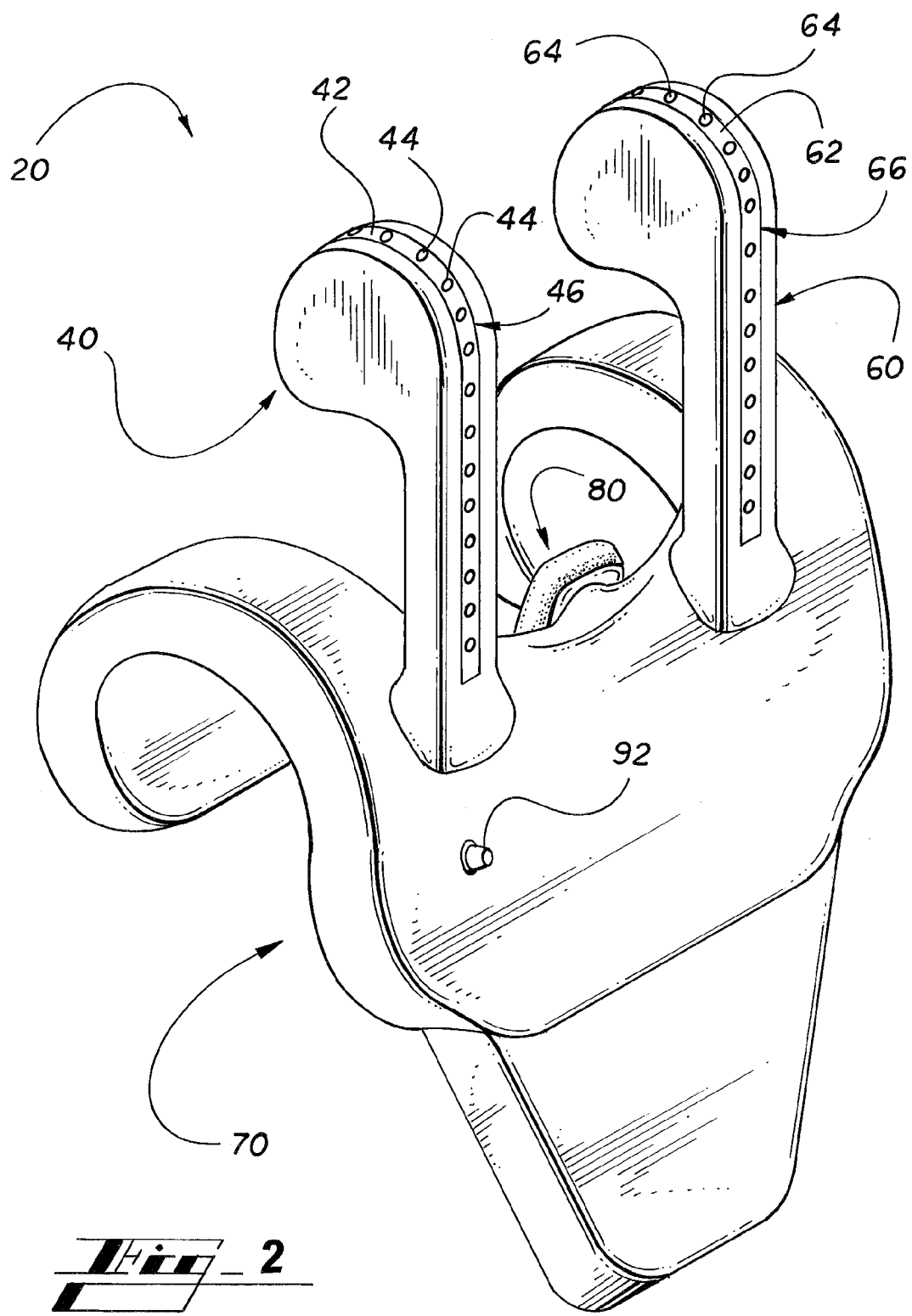
FIG. 2 is a perspective illustration of an exemplary embodiment of an apparatus for administering pain relief including features for comfort and aesthetics, according to the present invention.

Referring first to FIGS. 1 and 2 simultaneously, therein are shown exemplary embodiments of an apparatus 20 for administering pain relief in accordance with the present invention. The distinction between FIG. 1 and FIG. 2 is that FIG. 2 includes comfort padding for an individual and some aesthetic features that at least partially obscure some of the features of the invention. A pair of quartz crystals 30, 32 is disposed proximate a vibratory element 34. The vibratory element 34 is disposed mediate the crystals 30, 32. The combination of crystals 30, 32 and vibratory element 34 is secured in a support structure 40 so that the combination may be positioned proximate an individual to administer pain relief. The support structure may be a single unit that may be held in the hand or that may be a mountable structure as illustrated, either of which is able to be positioned proximate an individual so as to administer pain relief. An energizable lighting structure (which may alternatively be considered an energizable illuminating structure) 46 includes a strip 42 of a series of substantially linearly-aligned illuminating elements 44 disposed at least partially around the crystals 30, 32 and vibratory element 34 in an arced configuration. A second set of crystals 50, 52 and vibratory element is secured in a second support structure 60. A second energizable lighting structure (which may also alternatively be considered an illuminating structure) 66 includes a second strip 62 of a series of substantially linearly aligned illuminating elements 64 disposed at least partially around the second set of crystals 50, 52 and vibratory element 54 in an arced configuration.

Although each support structure 40, 60 may comprise tower-like components that are independent of one another, in the exemplary embodiment illustrated, each tower support structure 40, 60 is joined to a shoulder support 72 of a harness structure 70. The shoulder support 72 is a yoke-like device. A back brace 74 extends from the shoulder support 72. A switch 80 having a plunger activation mechanism 82 is disposed at the back of the shoulder support 72 to facilitate a particular method of operation that is described below. An electronic control box 90 provides an interconnection between each energizable vibratory element 34, 54 and an energizing source such as a battery or electrical adapter supplying direct current through known electronic connecting circuits. The control box 90 also provides interconnection between each energizable lighting structure 46, 66 and an energizing source such as a battery or electrical adapter supplying direct current through known electronic connecting circuits. A switch 92, in conjunction with known electronic circuit components and methodologies, is used for closing the circuits between the various vibratory elements and the lighting structures with respect to the energizing component so as to activate the vibratory elements and lighting structures.

The invention generally teaches a method of use comprising placing an arrangement of at least one quartz crystal disposed in proximate relationship to an energized vibratory element proximate the head region of an individual. The vibratory element may be energized prior to or after positioning of the apparatus proximate the head region of an individual. The quartz-crystal-and-vibratory-element combination may then be held at a predetermined position until relief is realized or for a predetermined period of time.

Referring now to FIG. 3, therein is illustrated an exemplary embodiment of a method for administering pain relief employing the exemplary apparatus 20 for administering pain relief of FIGS. 1 and 2. The apparatus 20 is positioned upon the shoulders of an individual 1 by means of the shoulder harness 70. The back brace 74 helps steady the apparatus 20 upon the shoulders of an individual and thereby helps maintain positioning of the tower support structures. The upper terminal region of the tower support structures 40, 60 (which house the crystals and vibratory element) are disposed upon either side of an individual's head 3. The methodology generally taught by the invention encompasses energizing the vibratory elements 34, 54 and lighting structures when the apparatus 20 is generally disposed upon the shoulders of an individual 1 with the crystals and vibratory elements positioned proximate the head region 3 of an individual. Another aspect of an exemplary methodology taught by the invention includes having the individual 1 tilt his or her head rearward so as to depress and maintain engagement with the plunger activation mechanism 82 of the lighting structure switch 80. The plunger mechanism 82 may be disposed and the methodology applied in a manner such that the plunger mechanism 82 is contacted substantially by the base of the head 3 or the upper region of the nape of the neck of a user 1. Although several angles of inclination (as measured from an imaginary vertical line extending through the top of the head of an individual up to slightly less than 90 degrees are effective, the invention teaches in particular an alignment whereby the head of the individual is tilted rearward at an angle of about 45 degrees. Although the lighting structures 46, 66 may be generally activated by the main control switch 92, the plunger switch mechanism 82 may serve as the final connecting and activating link. In addition, the lighting structure may be energized prior to placement of the apparatus proximate the head region of an individual. An individual can energize each lighting structure 46, 66 by engaging the plunger-type element 82 of the switch 80 from either a standing, sitting or reclined position. The methodology may generally be applied until relief from headache pain is realized, or the methodology may be employed for a defined period of time such as from about three minutes to about five minutes. The methodology may be applied for recommended periods of time to address specific ailments. For example, application of the methodology described above for less than three minutes may be used to provide relief from pain and discomfort due to sinus congestion. Application of the methodology from about four minutes to about five minutes may be used to provide relief from menstrual cramps. Although the invention may be practiced through simple activation of the energizable vibratory elements 34, 54 and lighting structures 46, 66, an enhanced mode of operation teaches an individual tilting his or her head rearward so as to engage and maintain depression of the plunger mechanism 82 for a pre-determined period of time or until relief is realized.

A typical energizing power source such as a direct-current battery pack may be placed in a suitable location such as upon the shoulder support 72 or back brace 74. A battery source may also be placed within the control box 90 for convenience. An adapter that converts alternating current to direct current and then supplies converted direct current by known means sufficient to energize the vibratory elements and lighting structures may also be employed.

A suitable quartz stone 30, 32, 50, 52 for the invention is quartz rock found in the area of Hot Springs, Ark., in relatively readily available quantities. A suitable configuration is a stone that is about 1½ ounces to about 2 ounces in weight and/or having geometric dimensions of about 1½ inches to about 2 inches in length and about 1 inch to about 2 inches in width or diameter.

A suitable vibratory element 34, 54 is a low-voltage, direct-current, eccentric-type motor, for example a 3-volt, miniature DC motor with eccentric shaft feature. The eccentric shaft feature creates a vibratory effect. A particular example of such a motor can be found in the product know as the Micro Tinglers Noiseless Massagers bullet type massager sold by California Exotics Novelties company of California. The vibratory element may be operated continuously or intermittently. The intensity, or frequency, of the vibratory element may be selectively variable, and the vibratory element may be operated at its highest intensity or frequency or at its lowest operable intensity or frequency, or at various settings in between the two extremes to provide relief.

A suitable energizable lighting structure 66 is a lighting strip. A suitable product that may be adapted for use in the invention is a lighting strip sold by Pilot Automotive, Inc. of City of Industry California under the product description "10" L.E.D. FLEXI-LITE," also having product identifier "CZ-180W."

The crystals 30, 32, 50, 52 and vibratory elements 34, 54 may be secured to each tower support structure by conventional mechanical means such as, but not limited to, use of an adhesive. The tower support structures 40, 60 are suitably sized and may be adjustable so as to facilitate positioning the operating elements proximate the region of a head 3 of an individual 1. For example, the tower support members 40, 60 may be made of flexible material such as bendable aluminum that can be bent so as to selectively position the quartz-crystal-and-vibratory-element combination proximate the head region of an individual.

The above-described embodiments are merely exemplary illustrations of implementations set forth for a clear understanding of the principles of the invention. Variations, modifications, and combinations may be made to the above-described embodiments without departing from the scope of the claims. For example, the teachings of the invention encompass the use of a single quartz crystal or more than two quartz crystals in association with a vibratory element. The teachings of the invention also encompass placement of a single arrangement proximate the head region of an individual and is not limited to a pair of opposing arrangements. All such variations, modifications, and combinations are included herein by the scope of this disclosure and the following claims.

What is claimed is:

1. An apparatus for administering pain relief comprising:
at least one quartz crystal disposed proximate an energizable vibratory element; and
a structure having a distal end that extends above a shoulder region of an individual to a height of an upper head region of the individual when in use, the distal end containing said at least one quartz crystal and said energizable vibratory element for positioning said at least one quartz crystal and said energizable vibratory element adjacent but in non-contacting and non-obstructing relationship with respect to the upper head region of the individual whereby the upper head region of the individual is adapted to be selectively movable between a first position of alignment and a plurality of alternative positions of alignment with respect to said structure, said at least one quartz crystal and said energizable vibratory element.

2. The apparatus of claim 1, wherein said structure comprises a shoulder harness having at least one extension comprising said distal end containing said at least one quartz crystal and said energizable vibratory element for positioning said extension, said at least one quartz crystal and said energizable vibratory element adjacent but in non-contacting and non-obstructing relationship with respect to the upper head region of the individual.

3. The apparatus of claim 1, wherein said at least one quartz crystal comprises a pair of quartz crystals.

4. The apparatus of claim 3, wherein said energizable vibratory element is disposed mediate said pair of quartz crystals.

5. The apparatus of claim 1, further comprising an energizable illuminating structure disposed proximate said at least one quartz crystal and said energizable vibratory element.

6. The apparatus of claim 5, wherein said energizable illuminating structure comprises a substantially elongated lighting strip.

7. The apparatus of claim 6, wherein said substantially elongated lighting strip is disposed in an arced relationship with respect to said at least one quartz crystal and said energizable vibratory element.

8. A method for administering pain relief comprising the steps of:
providing an apparatus comprising a structure having a distal end that extends above a shoulder region of an individual to a height of an upper head region of the individual when in use, the distal end containing at least one quartz crystal disposed proximate an energizable vibratory element;
positioning said structure, said at least one quartz crystal and said energizable vibratory element adjacent but in non-contacting and non-obstructing relationship with respect to the upper head region of the individual whereby the upper head region of the individual is selectively movable between a first position of alignment and a plurality of alternative positions of alignment with respect to said structure, said at least one quartz crystal and said energizable vibratory element; and
energizing said energizable vibratory element.

9. The method of claim 8, wherein the step of providing an apparatus further comprises providing a shoulder harness having at least one extension comprising said distal end containing said at least one quartz crystal and said energizable vibratory element and for positioning said extension, said at least one quartz crystal and said energizable vibratory element adjacent but in non-contacting and non-obstructing relationship with respect to the upper head region of the individual.

10. The method of claim 8, wherein the step of providing an apparatus comprising a structure containing at least one quartz crystal disposed proximate an energizable vibratory element further comprises providing a pair of quartz crystals disposed proximate said energizable vibratory element.

11. The method of claim 10, wherein the step of providing a pair of quartz crystals further comprises providing said pair of quartz crystals wherein said energizable vibratory element is mediately disposed therebetween.

12. The method of claim 8, wherein the step of providing an apparatus further comprises providing an energizable illuminating structure disposed proximate said at least one quartz crystal and said energizable vibratory element and the method further comprises the step of selectively energizing said energizable illuminating structure.

13. The method of claim 12, wherein the step of providing an energizable illuminating structure comprises providing a substantially elongated lighting strip proximate said at least one quartz crystal and said energizable vibratory element.

14. The method of claim 13, wherein the step of providing a substantially elongated lighting strip comprises providing said substantially elongated lighting strip disposed in an arced relationship with respect to said at least one quartz crystal and said energizable vibratory element.

15. An apparatus for administering pain relief comprising:
a first arrangement of
at least one quartz crystal disposed proximate an energizable vibratory element, and
a first structural element having a distal end that extends above a shoulder region of an individual to a height of an upper head region of the individual when in use, the distal end containing said at least one quartz crystal and said energizable vibratory element for positioning said at least one quartz crystal and said energizable vibratory element adjacent but in non-contacting and non-obstructing relationship with respect to the upper head region of the individual; and
a second arrangement of
at least one quartz crystal disposed proximate an energizable vibratory element, and
a second structural element having a distal end that extends above the shoulder region of the individual to a height of the upper head region of the individual when in use, the distal end of the second structural element containing said at least one quartz crystal and said energizable vibratory element for positioning said at least one quartz crystal and said energizable vibratory element adjacent but in non-contacting and non-obstructing relationship with respect to the upper head region of the individual;
wherein said first structural element and said second structural element are spaced apart from one another so as to receive the upper head region of the individual therebetween in non-contacting and non-obstructing relationship with respect to said first structural element, respective said at least one quartz crystal and respective said energizable vibratory element and said second structural element, respective said at least one quartz crystal and respective said energizable vibratory element whereby the upper head region of the individual is adapted to be selectively movable between a first position of alignment and a plurality of alternative positions of alignment with respect to said first structural element and respective said at least one quartz crystal and respective said energizable vibratory element and said second structural element and respective said at least one quartz crystal and respective said energizable vibratory element.

16. The apparatus of claim 15, further comprising a shoulder harness supporting said first structural element and said second structural element.

17. The apparatus of claim 16, further comprising an energizable illuminating structure disposed adjacent each respective said first arrangement and said second arrangement and a switch disposed upon said shoulder harness mediate said first structural element and said second structural element for selectively causing said energizable illuminating structures to become energized.

18. The apparatus of claim 15, wherein said at least one quartz crystal comprises a pair of quartz crystals.

19. The apparatus of claim 18, wherein said energizable vibratory element is disposed mediate said pair of quartz crystals.

20. The apparatus of claim 15, further comprising an energizable illuminating structure disposed adjacent each respective said first arrangement and said second arrangement.

21. The apparatus of claim 20, wherein said energizable illuminating structure comprises a substantially elongated lighting strip.

22. The apparatus of claim 21, wherein said substantially elongated lighting strip is disposed in an arced relationship with respect to said at least one quartz crystal and said energizable vibratory element.

23. A method for administering pain relief comprising the steps of:
providing an apparatus comprising
  a first arrangement of
    at least one quartz crystal disposed proximate an energizable vibratory element, and
    a first structural element having a distal end that extends above a shoulder region of an individual to a height of an upper head region of the individual when in use, the distal end containing said at least one quartz crystal and said energizable vibratory element for positioning said at least one quartz crystal and said energizable vibratory element adjacent but in non-contacting and non-obstructing relationship with respect to the upper head region of the individual; and
  a second arrangement of
    at least one quartz crystal disposed proximate an energizable vibratory element, and
    a second structural element having a distal end that extends above the shoulder region of the individual to the height of the upper head region of the individual when in use, the distal end of the second structural element containing said at least one quartz crystal and said energizable vibratory element for positioning said at least one quartz crystal and said energizable vibratory element adjacent but in non-contacting and non-obstructing relationship with respect to the upper head region of the individual;
a shoulder harness supporting said first structural element and said second structural element in spaced-apart relationship with respect to one another;
mounting said shoulder harness upon the individual so as to position said first arrangement and said second arrangement on opposing sides of the upper head region of the individual in non-contacting and non-obstructing relationship with respect to said first structural element, respective said at least one quartz crystal and respective said energizable vibratory element and said second structural element, respective said at least one quartz crystal and respective said energizable vibratory element; and
energizing said energizable vibratory elements.

24. The method of claim 23, wherein the step of providing an apparatus comprising a first arrangement of at least one quartz crystal and a second arrangement of at least one quartz crystal comprises the first arrangement of a pair of quartz crystals and the second arrangement of a pair of quartz crystals.

25. The method of claim 24, wherein in the step of providing an apparatus comprising a first arrangement of a pair of quartz crystals and a second arrangement of a pair of quartz crystals each respective said energizable vibratory element is disposed mediate each respective said pair of quartz crystals.

26. The method of claim 23, wherein the step of providing an apparatus further comprises providing an energizable illuminating structure disposed proximate each respective said first arrangement and said second arrangement and the method further comprises the step of selectively energizing said energizable illuminating structure.

27. The method of claim 26, wherein the step of providing an energizable illuminating structure comprises providing a substantially elongated lighting strip.

28. The method of claim 27, wherein the step of providing a substantially elongated lighting strip comprises providing said substantially elongated lighting strip disposed in an arced relationship with respect to said at least one quartz crystal and said energizable vibratory element.

* * * * *